United States Patent
Sakaguchi (10) Patent No.: US 10,709,423 B2
(45) Date of Patent: Jul. 14, 2020

(54) ULTRASOUND PROCESSING APPARATUS AND METHOD

(71) Applicant: SONY CORPORATION, Tokyo (JP)

(72) Inventor: Tatsumi Sakaguchi, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 801 days.

(21) Appl. No.: 14/782,990

(22) PCT Filed: Apr. 9, 2014

(86) PCT No.: PCT/JP2014/060266
§ 371 (c)(1),
(2) Date: Oct. 7, 2015

(87) PCT Pub. No.: WO2014/175068
PCT Pub. Date: Oct. 30, 2014

(65) Prior Publication Data
US 2016/0317128 A1 Nov. 3, 2016

(30) Foreign Application Priority Data
Apr. 22, 2013 (JP) .................................. 2013-089348

(51) Int. Cl.
*A61B 8/08* (2006.01)
*G01S 7/52* (2006.01)
(Continued)

(52) U.S. Cl.
CPC .............. *A61B 8/5223* (2013.01); *A61B 8/08* (2013.01); *A61B 8/12* (2013.01); *A61B 8/469* (2013.01);
(Continued)

(58) Field of Classification Search
CPC ............. G01S 15/8915; G01S 7/52042; A61B 8/5223; A61B 8/469; A61B 8/12;
(Continued)

(56) References Cited

U.S. PATENT DOCUMENTS 4,989,588 A * 2/1991 Kubota ............ A61B 17/22012
601/4
6,511,427 B1 * 1/2003 Sliwa, Jr. ............. A61B 5/4869
600/438
(Continued)

FOREIGN PATENT DOCUMENTS

CN          101242782 A       8/2008
CN          102641137 A       8/2012
(Continued)

OTHER PUBLICATIONS

Office Action for CN Patent Application No. 201480021427.8, dated Jan. 2, 2018, 08 pages of Office and 09 pages of English Translation.

(Continued)

*Primary Examiner* — Peter Luong
(74) *Attorney, Agent, or Firm* — Chip Law Group (57) ABSTRACT

The present disclosure relates to an ultrasound processing apparatus and method, and a program that enable easy and stable measurement of tissue characteristics. A vibrator driving unit drives a vibrator incorporated in an ultrasound probe based on a vibration parameter from a vibrator control unit. The vibrator control unit supplies a vibration parameter that is set in accordance with an indication signal input via a user interface, distribution information of viscoelastic coefficients, which is a measurement result of strain computed by a strain computation unit, or the like, and controls the vibrator driving unit. The present disclosure can be applied to, for example, an ultrasound diagnostic imaging apparatus that generates an ultrasound image based on a signal from a probe that captures an ultrasound image, and displays the ultrasound image.

12 Claims, 8 Drawing Sheets

(51) Int. Cl.
*G01S 15/89* (2006.01)
*A61B 8/12* (2006.01)
*A61B 8/00* (2006.01)

(52) U.S. Cl.
CPC .......... *A61B 8/485* (2013.01); *G01S 7/52042* (2013.01); *G01S 15/8915* (2013.01); *A61B 8/4444* (2013.01); *A61B 8/461* (2013.01)

(58) Field of Classification Search
CPC .......... A61B 8/485; A61B 8/08; A61B 8/461; A61B 8/4444
See application file for complete search history.

(56) References Cited

U.S. PATENT DOCUMENTS

| | | | |
|---|---|---|---|
| 9,060,670 B1 * | 6/2015 | Boctor | A61N 7/02 |
| 2002/0040187 A1 * | 4/2002 | Alam | A61B 5/0053 |
| | | | 600/442 |
| 2004/0079155 A1 * | 4/2004 | Omata | A61B 5/0051 |
| | | | 73/573 |
| 2005/0119568 A1 | 6/2005 | Salcudean et al. | |
| 2010/0217125 A1 | 8/2010 | Kadokura et al. | |
| 2010/0286518 A1 * | 11/2010 | Lee | A61B 8/4427 |
| | | | 600/439 |
| 2015/0141821 A1 * | 5/2015 | Yoshikawa | A61B 8/5207 |
| | | | 600/438 |

FOREIGN PATENT DOCUMENTS

| | | |
|---|---|---|
| JP | 2000-060853 A | 2/2000 |
| JP | 2004-223265 A | 8/2004 |
| JP | 2006-247214 A | 9/2006 |
| JP | 2008-301856 A | 12/2008 |
| JP | 2009-504217 A | 2/2009 |
| JP | 2009504217 A | 2/2009 |
| JP | 2009-531101 A | 9/2009 |
| JP | 2009531101 A | 9/2009 |
| JP | 2011-004806 A | 1/2011 |
| JP | 2011-067670 A | 4/2011 |
| JP | 2012-170823 A | 9/2012 |
| JP | 2012-249776 A | 12/2012 |

OTHER PUBLICATIONS

Office Action for JP Patent Application No. 2015-513670, dated Dec. 21, 2017, 04 pages of Office Action and 03 pages of English Translation.

Office Action for JP Patent Application No. 2015-513670, dated Jun. 12, 2018, 04 pages of Office Action and 03 pages of English Translation.

Office Action for JP Patent Application No. 2015-513670, dated Aug. 21, 2018, 09 pages of Office Action and 03 pages of English Translation.

* cited by examiner

ULTRASOUND PROCESSING APPARATUS AND METHOD

TECHNICAL FIELD

The present disclosure relates to an ultrasound processing apparatus and method, and a program, and particularly relates to an ultrasound processing apparatus and method, and a program that enable easy and stable measurement of tissue characteristics.

BACKGROUND ART

Static elastography using ultrasound is a technique of pressing a probe against a tissue to apply physical vibration, and displaying the degree (displacement and strain) of vibration as numerical values superimposed on an image. At present, a static elastography technique that is widely used clinically is a technique of vibrating a probe by hand.

This technique has difficulty in quantifying vibration (pressure). In addition, the direction of vibration does not coincide with an image surface, which results in incorrect elastography results, in some cases. Furthermore, this technique is difficult to apply especially to cases where the probe cannot be directly operated by hand, such as in laparoscopic surgery, for example.

Meanwhile, for example, Patent Literature 1 suggests implementation of elastography using a vibrator.

CITATION LIST

Patent Literature

Patent Literature 1: JP 2000-60853A

SUMMARY OF INVENTION

Technical Problem

Unfortunately, although the vibrator is vibrated in accordance with the output of a low-frequency oscillator according to Patent Literature 1, the control of the low-frequency oscillator is intended for switching between normal B-mode image acquisition and a signal acquisition mode during compression.

Furthermore, to measure the strain of a tissue, it is necessary for mechanical vibration to propagate to the target tissue part. On the other hand, too strong vibration (compression) lowers measurement accuracy.

The present disclosure, which has been made in view of such circumstances, enables easy and stable measurement of tissue characteristics.

Solution to Problem

According to an aspect of the present disclosure, there is provided an ultrasound processing apparatus including: a vibration control unit configured to set a vibration parameter of a vibration generating unit incorporated in a probe to vibrate the probe; and a vibration driving unit configured to drive the vibration generating unit based on the vibration parameter set by the vibrator control unit.

The vibrator control unit can set the vibration parameter in accordance with a user operation.

The user operation is setting of a focus position or setting of a region of interest (ROI).

A strain measurement unit configured to measure strain of an object based on an ultrasound signal acquired from a vibrating element of the probe can be further included. The vibrator control unit can set the vibration parameter in accordance with a result of the strain measured by the strain measurement unit.

The vibration parameter is a displacement, a vibration frequency, or a direction of a vibration.

The strain measurement unit can synchronize a timing of measurement of the strain with a vibration generated by the vibration generating unit.

A plurality of the vibration generating units are incorporated in the probe.

The probe is used in contact with an organ or a tissue during surgery.

According to an aspect of the present disclosure, there is provided an ultrasound processing method including: setting, by a ultrasound processing apparatus, a vibration parameter of a vibration generating unit incorporated in a probe to vibrate the probe; and driving, by the ultrasound processing apparatus, the vibration generating unit based on the set vibration parameter.

According to an aspect of the present disclosure, there is provided a program for causing a computer to function as: a vibration control unit configured to set a vibration parameter of a vibration generating unit incorporated in a probe to vibrate the probe; and a vibration driving unit configured to drive the vibration generating unit based on the vibration parameter set by the vibrator control unit.

According to an aspect of the present disclosure, a vibration parameter of a vibration generating unit incorporated in a probe is set in order to vibrate the probe. The vibration generating unit is driven based on the set vibration parameter.

Advantageous Effects of Invention

According to the present disclosure, tissue characteristics can be measured easily and stably.

DESCRIPTION OF EMBODIMENTS

Hereinafter, modes (hereinafter called embodiments) for carrying out the present disclosure will be described. The description is given in the following order.

1. First embodiment (ultrasound diagnostic imaging apparatus)
2. Second embodiment (computer)

First Embodiment

Example Configuration of Ultrasound Diagnostic Imaging Apparatus

Figure 1:
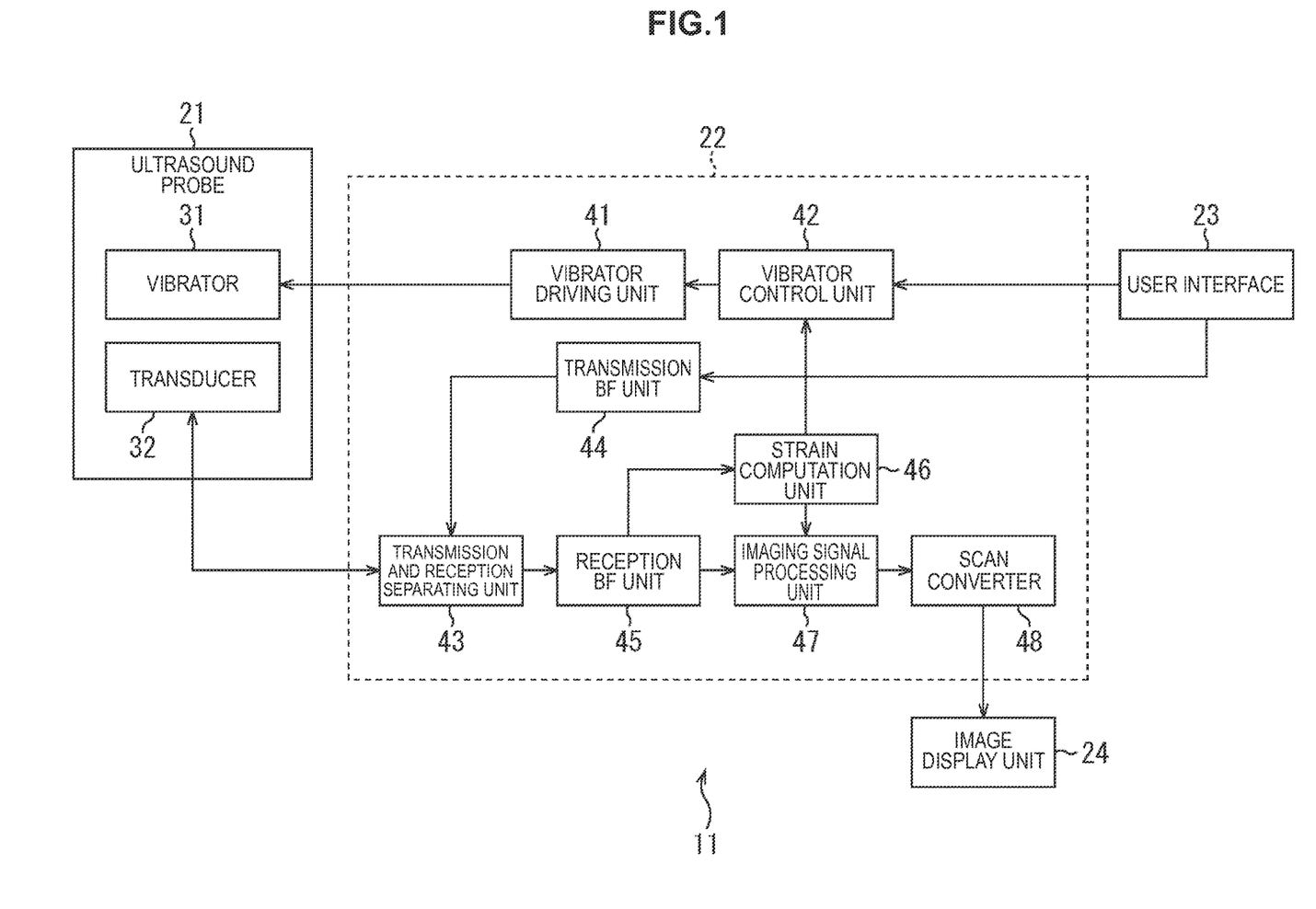
FIG. 1 is a block diagram illustrating an example configuration of an ultrasound diagnostic imaging apparatus to which the present technology is applied.

FIG. 1 illustrates an example configuration of an ultrasound diagnostic imaging apparatus as an ultrasound processing apparatus to which the present technology is applied.

An ultrasound diagnostic imaging apparatus 11 illustrated in FIG. 1 is an apparatus that captures an image (i.e., ultrasound image) of the inside of an object (target) by using ultrasound and displays the image. The ultrasound diagnostic imaging apparatus 11 is, for example, used for capturing images of the inside of a patient's body or a fetus or used in direct contact with an organ or a tissue during surgery in medical care, or used for capturing images of cross sections of the inside of a product in industry.

The ultrasound diagnostic imaging apparatus 11 includes an ultrasound probe 21, an ultrasound signal processing unit 22, a user interface 23, and an image display unit 24.

The ultrasound probe 21, which is a part that is pressed against an object (a living body (e.g., skin)) or the like to capture an image of the object, includes a vibrator 31 and a transducer 32. The ultrasound probe 21 may be a 1D array or a 2D array.

The vibrator 31, which is a vibration generating unit (eccentric motor) that is incorporated in the ultrasound probe 21 to vibrate the ultrasound probe 21, is driven by a vibrator driving unit 41 of the ultrasound signal processing unit 22. Note that the vibration generating unit is not limited to a vibrator, and any kind of vibration generating unit that has directivity and can have its rotation controlled is preferably used. The number of the vibrators 31 is not limited to one. Since the applied force changes depending on the weight of an eccentric weight, a plurality of vibration generating units (eccentric motors) with different sizes can be provided to allow control of various sizes. Alternatively, for example, a plurality of vibration generating units with different rotation directions may be incorporated.

The transducer 32 is configured with, for example, an array vibrating element in which a plurality of vibrating elements are arranged, the vibrating elements being arranged on the side in contact with the object. The transducer 32 emits an ultrasound beam to the object based on an ultrasound signal from a transmission and reception separating unit 43 of the ultrasound signal processing unit 22. In addition, the transducer 32 receives reflected waves from the object (a signal that is reflected and diffused by the object) and supplies the received signal to the transmission and reception separating unit 43.

The ultrasound signal processing unit 22 includes the vibrator driving unit 41, a vibrator control unit 42, the transmission and reception separating unit 43, a transmission BF unit 44, a reception BF unit 45, a strain computation unit 46, an imaging signal processing unit 47, and a scan converter 48.

The vibrator driving unit 41 is a vibration driving unit that drives the vibration of the vibrator 31. The vibrator driving unit 41 drives the vibrator 31 incorporated in the ultrasound probe 21 based on a vibration parameter from the vibrator control unit 42.

The vibrator control unit 42 is a vibration control unit that controls the vibration of the vibrator 31. The vibrator control unit 42 supplies a vibration parameter set in advance to the vibrator driving unit 41 to control the vibrator driving unit 41.

Alternatively, the vibrator control unit 42 sets or adjusts the vibration parameter in accordance with an indication signal (e.g., a region of interest (ROI) or the depth of focus in a depth direction) input via the user interface 23, distribution information of viscoelastic coefficients, which is a measurement result of strain computed by the strain computation unit 46, or the like. The vibrator control unit 42 supplies the set or adjusted vibration parameter to the vibrator driving unit 41 to control the vibrator driving unit 41.

Examples of the vibration parameter include the displacement (intensity) of vibration, vibration frequency (also called frequency), and the direction of rotation (orientation of eccentricity). Note that a parameter other than these examples may be used. Although FIG. 1 illustrates an example in which the vibration generating unit is the vibrator 31, the vibration generating unit is not limited to a vibrator and it is possible to use any vibration generating unit that generates vibration of which the above vibration parameter can be controlled.

The transmission and reception separating unit 43 is a switch that switches transmission and reception of an ultrasound signal. The transmission and reception separating unit 43 receives an ultrasound signal from the transmission BF unit 44, and supplies the received ultrasound signal to the transducer 32. The transmission and reception separating unit 43 receives an ultrasound signal from the transducer 32, and supplies the received ultrasound signal to the reception BF unit 45.

The transmission BF unit 44 performs a transmission beamforming process, which is a process to generate an ultrasound signal (waveform), and outputs the signal after the transmission beamforming process to the transmission and reception separating unit 43.

The reception BF unit 45 performs a reception beamforming process on a signal received from the transmission and reception separating unit 43. The reception beamforming process is specifically the following process: based on a distance from a target point in a measuring area to the transducer 32 in the ultrasound probe 21, phases of received waves are matched through a process to add signals obtained by delaying each of the received waves of each vibrating element (hereinafter called phasing addition process as appropriate), and a reflected wave detection signal (hereinafter called RF signal) indicating the intensity of reflected waves from the target point in the measuring area is generated.

The reception BF unit 45 supplies the signal after the reception beamforming process (after the phasing addition) to the strain computation unit 46 and the imaging signal processing unit 47.

The strain computation unit 46 measures strain of the object (inside) including an inspection target by using the signal after the phasing addition from the reception BF unit 45. In other words, the strain computation unit 46 finds the distribution of viscoelastic coefficients from the signal after the phasing addition from the reception BF unit 45. The strain computation unit 46 supplies distribution information of viscoelastic coefficients, which is a result of strain measurement, to the vibrator control unit 42 and the imaging signal processing unit 47. In this specification, a viscoelastic coefficient does not mean a viscoelastic modulus itself but means any coefficient that indicates viscoelasticity.

The imaging signal processing unit 47 performs signal processing on the signal after the phasing addition from the reception BF unit 45 to convert the signal to a brightness image (brightness (B)-mode image). The imaging signal processing unit 47 superimposes the distribution information of viscoelastic coefficients on a B-mode image obtained by the conversion to generate a display image. The imaging signal processing unit 47 supplies the generated display image to the scan converter 48.

The scan converter 48 causes the image display unit 24 to display the display image from the imaging signal processing unit 47.

The user interface 23 is configured with, for example, a mouse or a keyboard. The user interface 23 supplies information corresponding to a user operation to the vibrator control unit 42 and the transmission BF unit 44.

The image display unit 24 is configured with, for example, a liquid crystal display (LCD), and displays the display image from the scan converter 48.

Here, methods for controlling the driving of the vibrator 31 include the following first to third methods.

The first method is a method of not performing control based on a user, i.e., a user-specified focus position or a region of interest (ROI), control using distribution information of viscoelastic coefficients, or the like.

The second method is a method of performing only control based on an ROI or a user-specified focus position. The third method is a method of performing control based on an ROI or a user-specified focus position and control using distribution information of viscoelastic coefficients.

Here, a focus in an ultrasound apparatus is set at any "depth" vertically below a vibrating element. Generally controlled is one depth within a screen, which is one-dimensional. The same definition applies to this specification. In contrast, an ROI in this specification indicates a specific region in a screen; controlled is a position within a screen (with respect to a lateral direction as well as depth), which is two-dimensional.

[Example of Ultrasound Signal Processing]

First, ultrasound signal processing in the case of performing vibrator control by the first method is described with reference to the flowchart in in FIG. 2. For example, described is vibrator control by a method of not performing control based on a user, i.e., an ROI, control using distribution information of viscoelastic coefficients, or the like.

In step S21, the vibrator control unit 42 and the transmission BF unit 44 wait until a strain measurement mode (also called elastography mode) is turned on. In response to an indication signal from a user input via the user interface 23, when it is determined that the strain measurement mode has been turned on in the vibrator control unit 42 in step S21, the processing proceeds to step S22.

The vibrator control unit 42 supplies a vibration parameter set in advance to the vibrator driving unit 41 in accordance with the indication signal input via the user interface 23. In response to this, in step S22, the vibrator driving unit 41 drives the vibrator 31 incorporated in the ultrasound probe 21 based on the vibration parameter from the vibrator control unit 42.

The transmission BF unit 44 starts the transmission beamforming process in accordance with the indication signal input via the user interface 23. In response to this, in step S23, the reception BF unit 45 acquires signals for two frames. The number of frames acquired here is at least two, and may be three or more.

Specifically, the transmission BF unit 44 performs a transmission beamforming process, which is a process to generate an ultrasound signal (waveform), in accordance with the indication signal input via the user interface 23, and outputs the signal after the transmission beamforming process to the transmission and reception separating unit 43.

The transmission and reception separating unit 43 receives the ultrasound signal from the transmission BF unit 44, and supplies the received ultrasound signal to the transducer 32.

The transducer 32 emits an ultrasound beam to the object based on the ultrasound signal from the transmission and reception separating unit 43. In addition, the transducer 32 receives reflected waves from the object (a signal that is reflected and diffused by the object) and supplies the received signal to the transmission and reception separating unit 43. The transmission and reception separating unit 43 receives the ultrasound signal from the transducer 32, and supplies the received ultrasound signal to the reception BF unit 45.

These processes are performed for two frames and thus the reception BF unit 45 acquires signals for two frames. The reception BF unit 45 performs a reception beamforming process on the signals for two frames, and supplies the signal after the process (after the phasing addition) to the strain computation unit 46 and the imaging signal processing unit 47.

In step S24, the strain computation unit 46 measures strain. In other words, the strain computation unit 46 finds the distribution of viscoelastic coefficients from the signal after the phasing addition from the reception BF unit 45, and supplies the found distribution information of viscoelastic coefficients to the imaging signal processing unit 47.

Frequency or the like can be controlled by the vibrator control unit 42; thus, the vibration of the vibration generating unit (vibrator) and the timing of strain measurement by the strain computation unit 46 can be synchronized. Strain measurement at a point without acceleration in vibration (timing at the turning point of vibration) is difficult to perform accurately. The synchronization can eliminate inaccurate measurement results.

In step S25, the imaging signal processing unit 47 performs B-mode imaging. In other words, the imaging signal processing unit 47 performs signal processing on the signal after the phasing addition from the reception BF unit 45 to convert the signal to a brightness image (B-mode image).

In step S26, the imaging signal processing unit 47 superimposes the distribution information (map) of viscoelastic coefficients on the B-mode image obtained by the conversion to generate a display image. In the elastography mode, the distribution information of viscoelastic coefficients may be superimposed on the B-mode image as an image in which different coefficients are colored in different colors, or numerical values of the distribution information may be superimposed on the B-mode image as they are to be displayed. The imaging signal processing unit 47 supplies the generated display image to the scan converter 48.

In step S27, the scan converter 48 causes the image display unit 24 configured with an LCD or the like to display the display image from the imaging signal processing unit 47.

Figure 2:
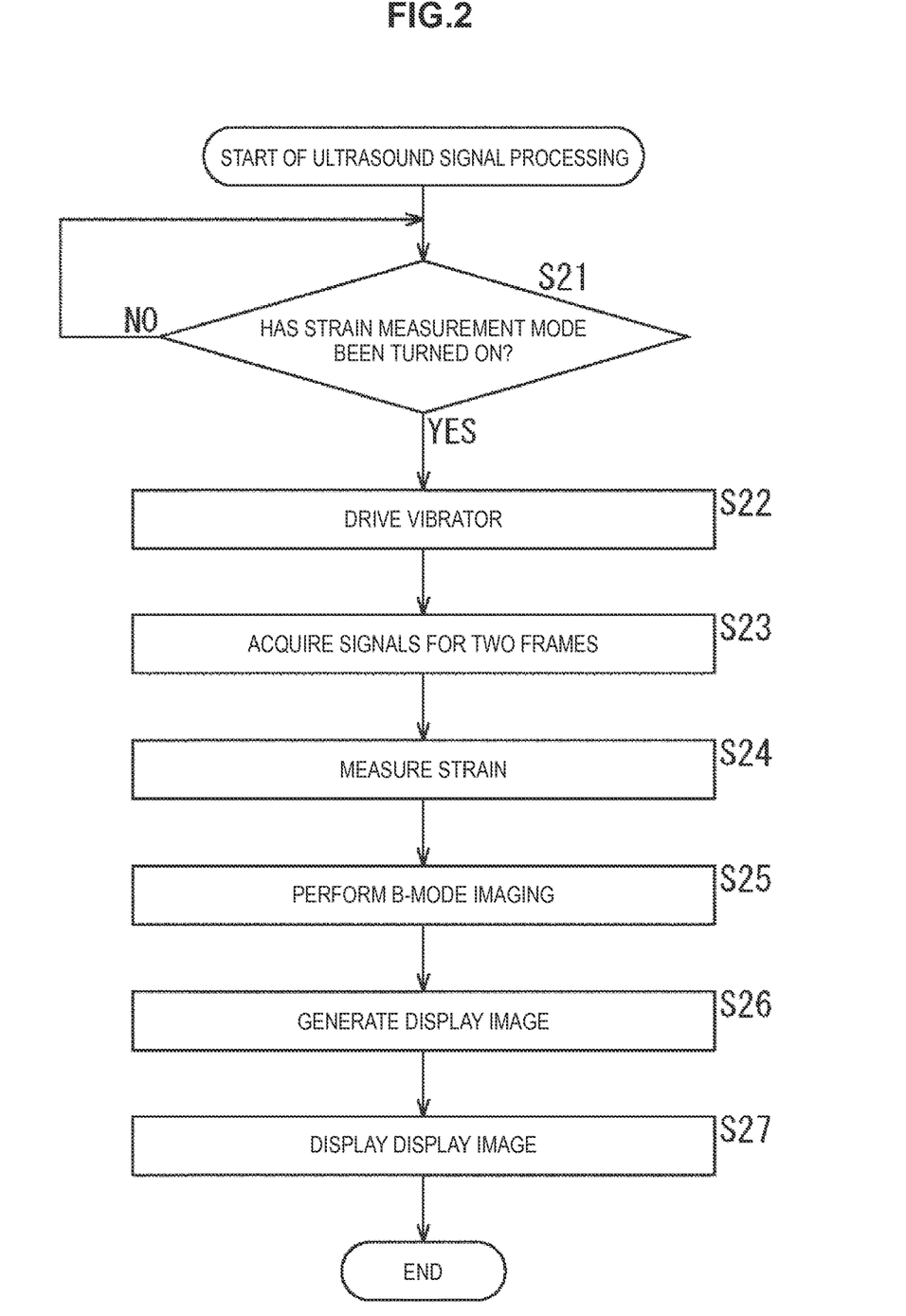
FIG. 2 is a flowchart for describing an example of ultrasound signal processing.

In the example of FIG. 2, in step S22, the driving of the vibrator is controlled based on the vibration parameter set in advance. Note that in this case, the driving may be controlled based on a parameter such as intensity or vibration frequency that is directly input via the user interface 23, instead of a vibration parameter set in advance.

[Another Example of Ultrasound Signal Processing]

Figure 3:
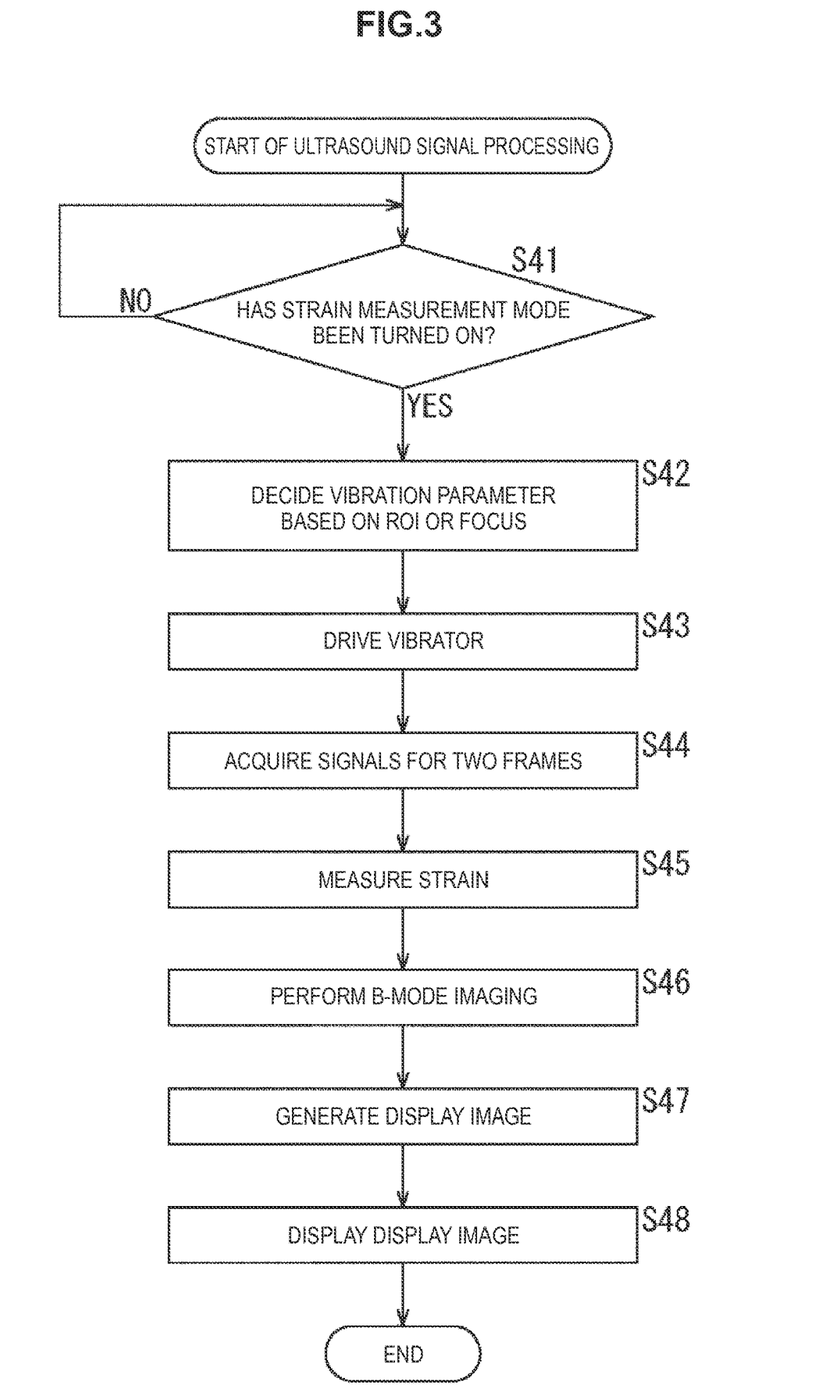
FIG. 3 is a flowchart for describing another example of ultrasound signal processing.

Next, ultrasound signal processing in the case of performing vibrator control by the second method is described with reference to the flowchart in in FIG. 3. In other words, described is a method of performing feedforward control based on a focus position or an ROI. Note that the processing of steps S41 and S43 to S48 in FIG. 3 is basically the same as that of steps S21 to S27 in FIG. 2 and detailed description of the processing is omitted.

In step S41, the vibrator control unit 42 and the transmission BF unit 44 wait until a strain measurement mode is turned on. In response to an indication signal from a user input via the user interface 23, when it is determined that the strain measurement mode has been turned on in the vibrator control unit 42 in step S41, the processing proceeds to step S42.

In step S42, the vibrator control unit 42 decides, in accordance with the indication signal input via the user interface 23, a vibration parameter based on the setting of an ROI or a focus position (including the depth of focus in a depth direction) specified by the user, and supplies the vibration parameter to the vibrator driving unit 41. In response to this, in step S43, the vibrator driving unit 41 drives the vibrator 31 incorporated in the ultrasound probe 21 based on the vibration parameter from the vibrator control unit 42.

The transmission BF unit 44 starts the transmission beamforming process in accordance with the indication signal input via the user interface 23. In response to this, in step S44, the reception BF unit 45 acquires signals for two frames.

In step S45, the strain computation unit 46 measures strain. In other words, the strain computation unit 46 finds the distribution of viscoelastic coefficients from the signal after the phasing addition from the reception BF unit 45, and supplies the found distribution information of viscoelastic coefficients to the imaging signal processing unit 47.

In step S46, the imaging signal processing unit 47 performs B-mode imaging. In other words, the imaging signal processing unit 47 performs signal processing on the signal after the phasing addition from the reception BF unit 45 to convert the signal to a brightness image (B-mode image).

In step S47, the imaging signal processing unit 47 superimposes the distribution information of viscoelastic coefficients on the B-mode image obtained by the conversion to generate a display image. The imaging signal processing unit 47 supplies the generated display image to the scan converter 48.

In step S48, the scan converter 48 causes the image display unit 24 configured with an LCD or the like to display the display image from the imaging signal processing unit 47.

As described above, in the ultrasound signal processing in FIG. 3, a vibration parameter group for driving the vibrator 31 is calculated from the state of an ROI or a focus position input by a user.

Accordingly, for example, the vibration can be controlled to be small when the focus position is shallow, and to be relatively large when the focus position is deep. In addition, for example, when the ROI is misaligned with the center of the transducer 32, eccentricity can be controlled (e.g., the direction of the vibration can be inclined toward the center of the ROI).

[Control of Eccentricity]

Next, control of eccentricity using the vibrator 31 is described with reference to FIGS. 4 to 6.

Figure 4:
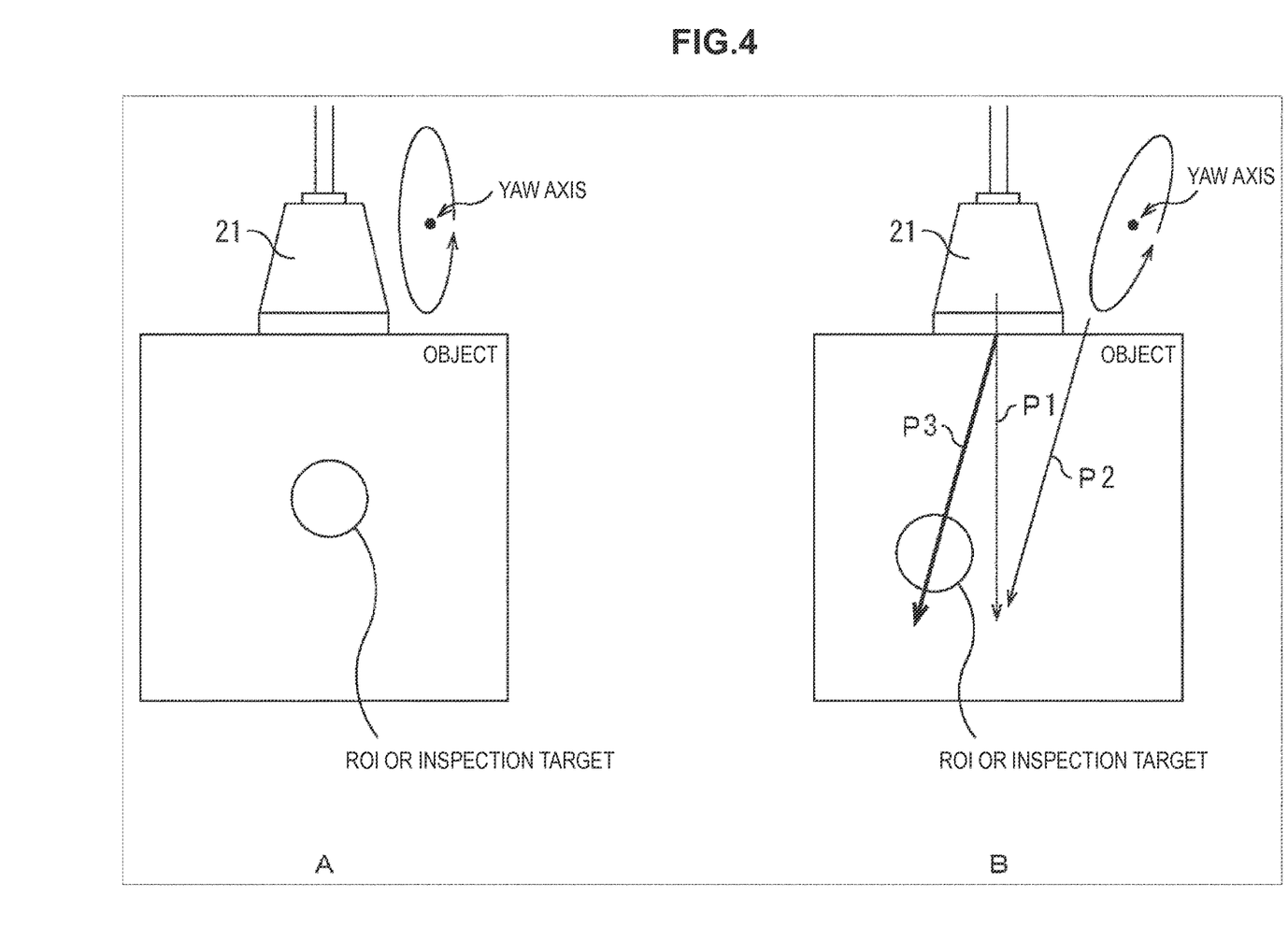
FIG. 4 is a view for describing control of eccentricity.

The example of FIG. 4 illustrates a state in which the ultrasound probe 21 that is a 1D or 2D array is in contact with an object, the state being viewed from a side surface where vibrating elements of the ultrasound probe 21 are arranged. The side surface where vibrating elements of the ultrasound probe 21 are arranged is a side surface of a long side in the case of a 1D array. That is, in the figure, vibrating elements are arranged from the left toward the right in the ultrasound probe 21.

The example of FIG. 4 illustrates the Yaw axis of the ultrasound probe 21. The Yaw axis is an axis that rotates parallel to the object when viewed from above the ultrasound probe 21. As illustrated in "A" of FIG. 4, the ultrasound probe 21 is generally placed right above an ROI or inspection target, so that a cross-sectional image of the ROI or inspection target can be acquired.

Here, when the ultrasound probe 21 is slightly misaligned with the position right above the ROI or inspection target as illustrated in "B" of FIG. 4, a cross-sectional image of the ROI or inspection target cannot be acquired. In addition, inclining the ultrasound probe 21 itself to incline the Yaw axis is not practical because that would bring a sensor surface (e.g., the left side portion of the sensor surface in the figure) of the ultrasound probe 21 out of contact with the object in some cases.

Therefore, the eccentricity of the Yaw axis is controlled in the following manner: the vibration parameter of the vibrator 31 is adjusted so that the Yaw axis in a state of being perpendicular to the ROI or inspection target, as indicated by an arrow P1, is inclined in a clockwise direction in the figure as indicated by an arrow P2. Thus, even if the ultrasound probe 21 is slightly misaligned with the position right above the ROI or inspection target as indicated by a thick arrow P3 in the figure, a cross-sectional image of the ROI or inspection target can be acquired.

Figure 5:
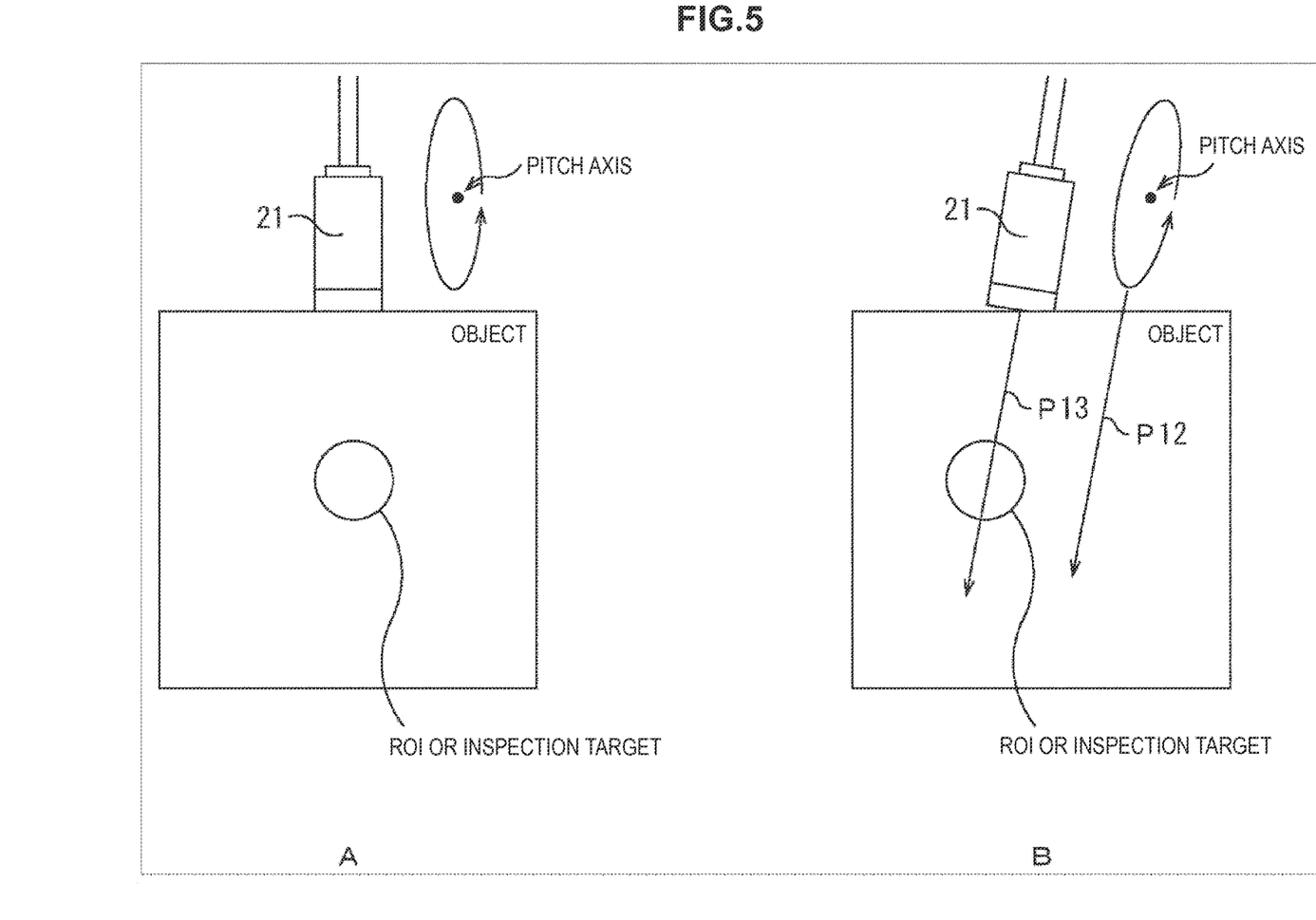
FIG. 5 is a view for describing control of eccentricity.

Next, the example of FIG. 5 illustrates a state in which the ultrasound probe 21 that is a 1D array is in contact with an object, the state being viewed from a side surface where vibrating elements of the ultrasound probe 21 are not arranged. The side surface where vibrating elements of the ultrasound probe 21 are not arranged is a side surface of a short side in the case of a 1D array. That is, in the figure, vibrating elements are arranged from the front toward the back in the ultrasound probe 21.

The example of FIG. 5 illustrates the Pitch axis of the ultrasound probe 21. The Pitch axis is an axis that rotates to-and-fro when viewed from a side surface of the ultrasound probe 21. As illustrated in "A" of FIG. 5, the ultrasound probe 21 is generally placed right above an ROI or inspection target, so that a cross-sectional image of the ROI or inspection target can be acquired.

Here, when the ultrasound probe 21 is slightly misaligned with the position right above the ROI or inspection target, a cross-sectional image of the ROI or inspection target cannot be acquired. However, unlike in the case of FIG. 4, regarding the Pitch axis, when a user inclines the ultrasound probe 21 itself with one's hand or the like, as illustrated in "B" of FIG. 5, even if the ultrasound probe 21 is slightly misaligned with the position right above the ROI or inspection target as indicated by a thick arrow P13 in the figure, a cross-sectional image of the ROI or inspection target can be acquired.

In other words, in the case of a 1D array, the inclination of the Pitch axis indicated by an arrow P12 always coincides with the inclination of the ultrasound probe 21 indicated by the thick arrow P13. This eliminates the need to change the inclination of the Pitch axis with respect to the ultrasound probe 21.

Figure 6:
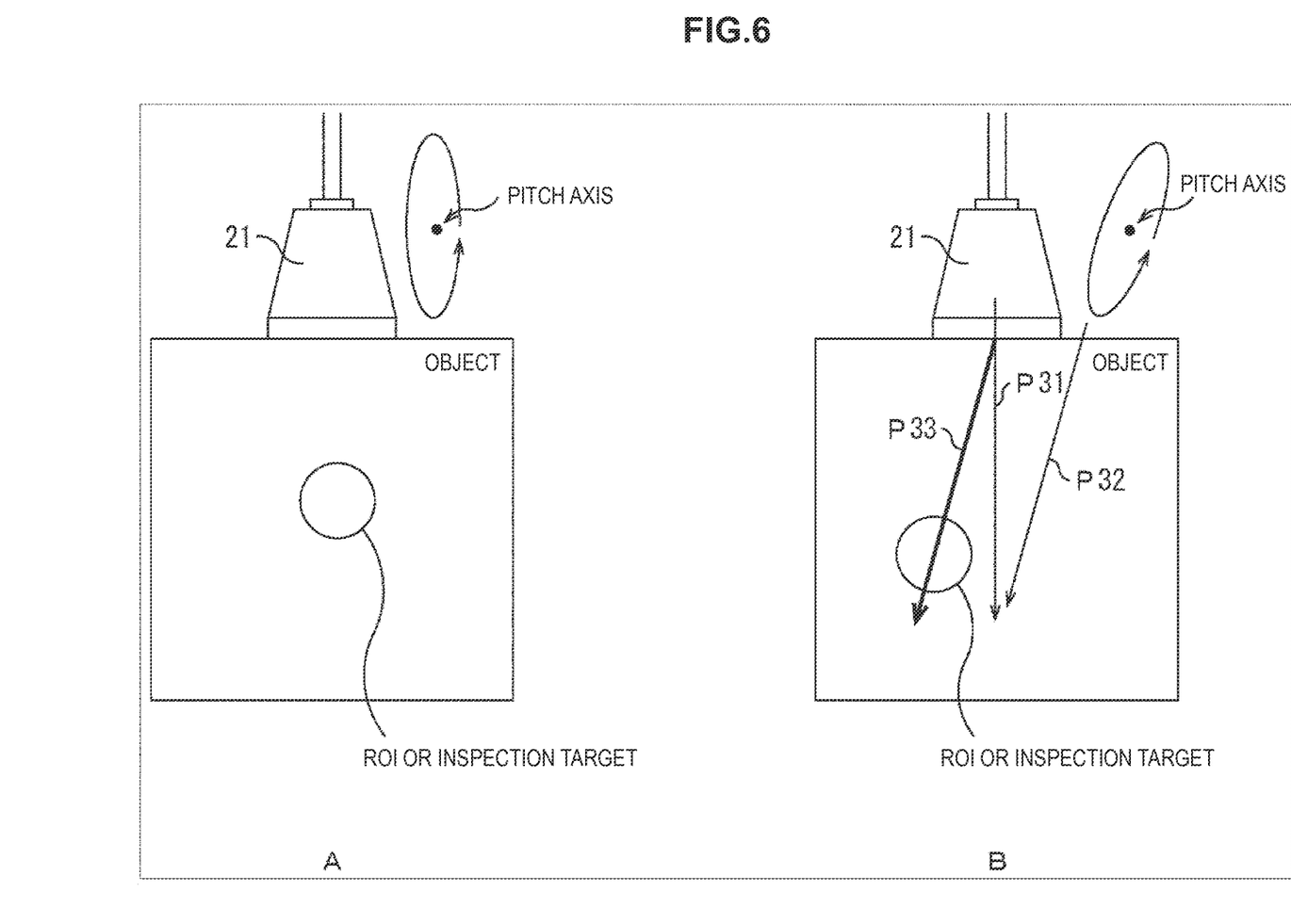
FIG. 6 is a view for describing control of eccentricity.

Furthermore, the example of FIG. 6 illustrates a state in which the ultrasound probe 21 that is a 2D array is in contact with an object, the state being viewed from the same side surface as in the example of FIG. 5. Since the ultrasound probe 21 is a 2D array, in the figure, vibrating elements are arranged from the front toward the back in the ultrasound probe 21, and are also arranged from the left toward the right.

The example of FIG. 6 illustrates the Pitch axis of the ultrasound probe 21. The Pitch axis is an axis that rotates to-and-fro when viewed from a side surface of the ultrasound probe 21. As illustrated in "A" of FIG. 6, the ultrasound probe 21 is generally placed right above an ROI or inspection target, so that a cross-sectional image of the ROI or inspection target can be acquired.

Here, when the ultrasound probe 21 is slightly misaligned with the position right above the ROI or inspection target as illustrated in "B" of FIG. 6, a cross-sectional image of the ROI or inspection target cannot be acquired. In addition, inclining the ultrasound probe 21 itself to incline the Pitch axis is not practical because that would bring a sensor surface (e.g., the left side portion of the sensor surface in the figure) of the ultrasound probe 21 out of contact with the object in some cases, because the ultrasound probe 21 is a 2D array.

Therefore, the eccentricity of the Pitch axis is controlled in the following manner: the Pitch axis in a state of being perpendicular to the ROI or inspection target, as indicated by an arrow P31, is inclined in a clockwise direction in the figure as indicated by an arrow P32.

In this case, unlike in the case of the Yaw axis in FIG. 4, it is necessary to also control the rotation axis (Pitch axis) of a vibration generating unit (i.e., the vibrator 31) for applying pressure. That is, in the example of FIG. 6, it is preferred to control at least two vibration generating units (i.e., the vibrators 31) for the Yaw axis and the Pitch axis.

In this manner, that is, by adjusting the orientation of the eccentricity of a vibration parameter, even if the ultrasound probe 21 is slightly misaligned with the position right above the ROI or inspection target as indicated by a thick arrow P33 in the figure, a cross-sectional image of the ROI or inspection target can be acquired.

[Another Example of Ultrasound Signal Processing]

Figure 7:
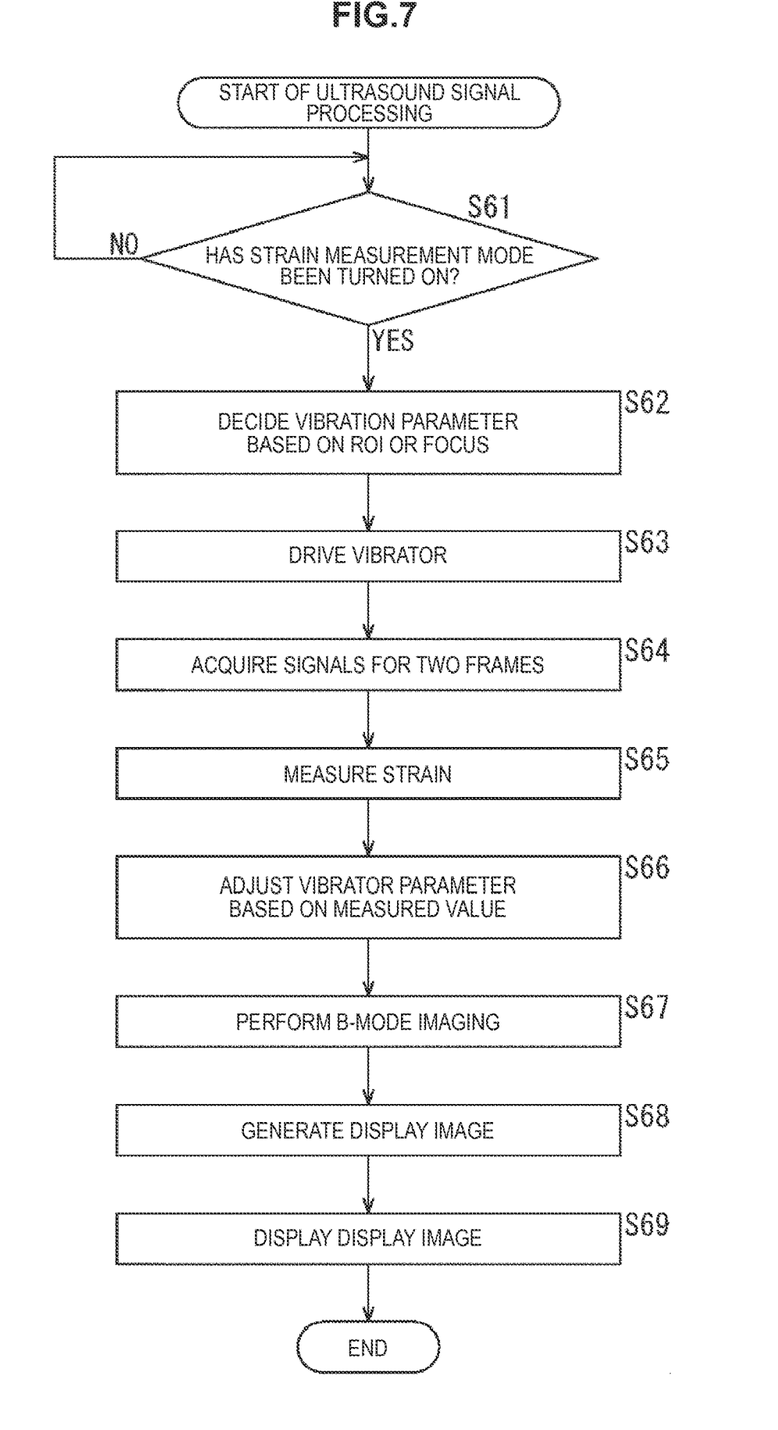
FIG. 7 is a flowchart for describing further another example of ultrasound signal processing.

Next, ultrasound signal processing in the case of performing vibrator control by the third method is described with reference to the flowchart in in FIG. 7. In other words, described is a method of performing feedforward control based on an ROI and feedback control using distribution information of viscoelastic coefficients. Note that the processing of steps S61, S63 to S65, and S67 to S69 in FIG. 7 is basically the same as that of steps S21 to S27 in FIG. 2 and detailed description of the processing is omitted.

In step S61, the vibrator control unit 42 and the transmission BF unit 44 wait until a strain measurement mode is turned on. In response to an indication signal from a user input via the user interface 23, when it is determined that the strain measurement mode has been turned on in the vibrator control unit 42 in step S61, the processing proceeds to step S62.

In step S62, the vibrator control unit 42 decides, in accordance with the indication signal input via the user interface 23, a vibration parameter based on the setting of an ROI or a focus position (including the depth of focus in a depth direction) specified by the user.

In step S63, the vibrator driving unit 41 drives the vibrator 31 incorporated in the ultrasound probe 21 based on the vibration parameter from the vibrator control unit 42. Note that the vibrator control unit 42 controls the vibrator driving unit 41 by using a parameter obtained by adjusting, in S66 which is described later, the vibration parameter decided in step S62.

The transmission BF unit 44 starts the transmission beamforming process in accordance with the indication signal input via the user interface 23. In response to this, in step S64, the reception BF unit 45 acquires signals for two frames.

In step S65, the strain computation unit 46 measures strain. In other words, the strain computation unit 46 finds the distribution of viscoelastic coefficients from the signal after the phasing addition from the reception BF unit 45, and supplies the found distribution information of viscoelastic coefficients to the vibrator control unit 42 and the imaging signal processing unit 47.

In step S66, the vibrator control unit 42 adjusts the vibration parameter based on a measured value. In other words, the vibrator control unit 42 adjusts the vibration parameter decided in step S62 in accordance with the distribution information of viscoelastic coefficients from the strain computation unit 46. The vibrator control unit 42 supplies the adjusted vibration parameter to the vibrator driving unit 41.

In step S67, the imaging signal processing unit 47 performs B-mode imaging. In other words, the imaging signal processing unit 47 performs signal processing on the signal after the phasing addition from the reception BF unit 45 to convert the signal to a brightness image (B-mode image).

In step S68, the imaging signal processing unit 47 superimposes the distribution information of viscoelastic coefficients on the B-mode image obtained by the conversion to generate a display image. The imaging signal processing unit 47 supplies the generated display image to the scan converter 48.

In step S69, the scan converter 48 causes the image display unit 24 configured with an LCD or the like to display the display image from the imaging signal processing unit 47.

As described above, in the ultrasound signal processing in FIG. 7, a parameter group for driving the vibrator 31 is adjusted based on distribution information of viscoelastic coefficients, which is a result of strain measurement.

For example, vibration intensity is gradually increased when the distribution information of viscoelastic coefficients of an ROI does not exhibit a significant distribution. It is also possible to monitor variations of strain and, control the vibration (e.g., gradually decrease vibration intensity in the case of a wide scatter) based on feedback of a strain result.

In the case of changing the intensity of vibration, conceivable methods are a method of synchronously controlling the rotation of the vibrator 31 (eccentric motor) and a method of mounting a plurality of motors equipped with weights having different weights or eccentricities in advance. When a controllable range of rotation control is exceeded, it is possible to perform a process such as switching to an eccentric motor that can produce a larger motion.

As described above, the present technology incorporates a vibration generating unit in a probe so that vibration can always be quantified and coincide with an image surface. This makes it possible to find viscoelastic coefficients more stably than by using a manual technique (a technique using hands).

The present technology can be applied to laparoscopic surgery, thoracoscopic surgery, and the like, which are difficult to carry out by a manual technique. That is, the above-described probe can be used in contact with an organ or a tissue during such surgery.

The intensity of vibration, frequency corresponding to tissue characteristics, or the like can be set appropriately in accordance with a user-specified ROI.

The intensity of vibration, frequency corresponding to tissue characteristics, or the like can be set appropriately by feedback control based on a strain measurement result.

Since frequency or the like can be controlled, the vibration of the vibration generating unit (vibrator) and the timing of strain measurement can be synchronized. Strain measurement at a point without acceleration in vibration (timing at the turning point of vibration) is difficult to perform accurately. Accordingly, for example, measurement is not performed at a zero acceleration point in the vibration but performed at a point with acceleration. Such synchronization can eliminate inaccurate measurement results.

According to the above description, the present technology makes it possible to measure tissue characteristics easily and stably with an ultrasound signal processing apparatus that is used during surgery. This allows, for example, support of the determination of a surgical form for segmental resection of a tissue or the like or the decision of the extent of resection.

The present technology can be used for both medical care purposes and non-medical care purposes. In the case of non-medical care purposes, it is preferred to, for example, allow the frequency and intensity of ultrasound to be adjusted appropriately so that a viscus or the like does not appear in the image.

Furthermore, the present technology can be used for animals, plants, and artifacts, for example, as well as human in various scenes where images of cross sections of objects are captured by using ultrasound.

The series of processes described above can be executed by hardware but can also be executed by software. When the series of processes is executed by software, a program that constructs such software is installed into a computer. Here, the expression "computer" includes a computer in which dedicated hardware is incorporated and a general-purpose personal computer or the like that is capable of executing various functions when various programs are installed.

Second Embodiment

Computer Configuration Example

Figure 8:
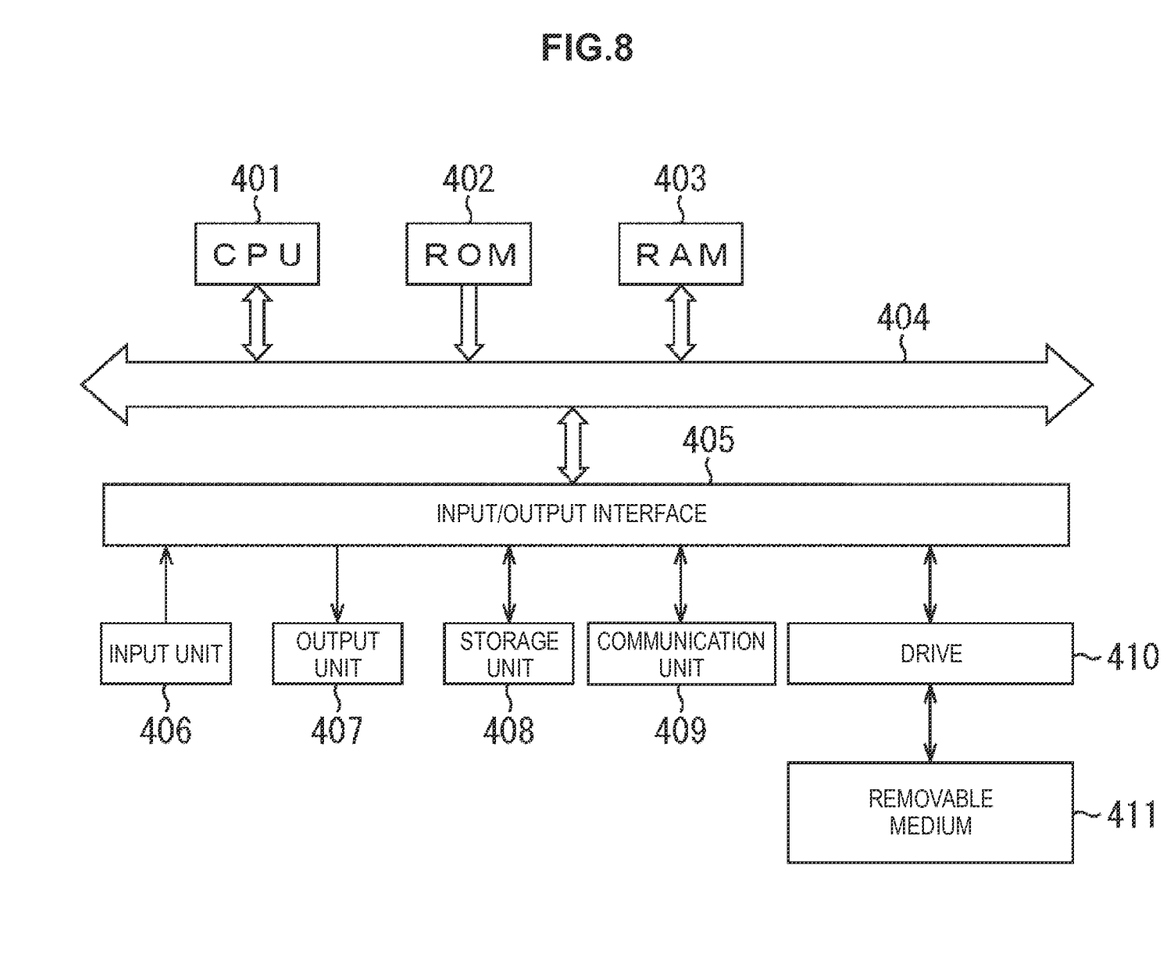
FIG. 8 is a block diagram illustrating an example configuration of a computer.

FIG. 8 is a block diagram showing an example configuration of the hardware of a computer that executes the series of processes described earlier according to a program.

In a computer, a CPU (Central Processing Unit) 401, a ROM (Read Only Memory) 402, and a RAM (Random Access Memory) 403 are mutually connected by a bus 404.

An input/output interface 405 is also connected to the bus 404. An input unit 406, an output unit 407, a storage unit 408, a communication unit 409, and a drive 410 are connected to the input/output interface 405.

The input unit 406 is configured from a keyboard, a mouse, a microphone or the like. The output unit 407 configured from a display, a speaker or the like. The storage unit 408 is configured from a hard disk, a non-volatile memory or the like. The communication unit 409 is configured from a network interface or the like. The drive 410 drives a removable medium 411 such as a magnetic disk, an optical disk, a magneto-optical disk, a semiconductor memory or the like.

In the computer configured as described above, as one example the CPU 401 loads a program stored in the storage unit 408 via the input/output interface 405 and the bus 404 into the RAM 403 and executes the program to carry out the series of processes described earlier.

As one example, the program executed by the computer (the CPU 401) may be provided by being recorded on the removable medium 411 as a packaged medium or the like. The program can also be provided via a wired or wireless transfer medium, such as a local area network, the Internet, or a digital broadcast.

In the computer, by loading the removable medium 411 into the drive 410, the program can be installed into the storage unit 408 via the input/output interface 405. It is also possible to receive the program from a wired or wireless transfer medium using the communication unit 409 and install the program into the storage unit 408. As another alternative, the program can be installed in advance into the ROM 402 or the storage unit 408.

Note that the program executed by the computer may be a program in which processes are carried out in a time series in the order described in this specification or may be a program in which processes are carried out in parallel or at necessary timing, such as when the processes are called.

Further, in this specification, the term "system" refers to a whole device composed of a plurality of devices, blocks, or means, for example.

An embodiment of the disclosure is not limited to the embodiments described above, and various changes and modifications may be made without departing from the scope of the disclosure.

The preferred embodiments of the present disclosure have been described above with reference to the accompanying drawings, whilst the disclosure is not limited to the above examples, of course. A person skilled in the art may find various alterations and modifications within the scope of the appended claims, and it should be understood that they will naturally come under the technical scope of the present disclosure.

Additionally, the present technology may also be configured as below.

(1)

An ultrasound processing apparatus including:
a vibration control unit configured to set a vibration parameter of a vibration generating unit incorporated in a probe to vibrate the probe; and
a vibration driving unit configured to drive the vibration generating unit based on the vibration parameter set by the vibrator control unit.

(2)

The ultrasound processing apparatus according to (1),
wherein the vibrator control unit sets the vibration parameter in accordance with a user operation.

(3)

The ultrasound processing apparatus according to (2),
wherein the user operation is setting of a focus position or setting of a region of interest (ROI).

(4)

The ultrasound processing apparatus according to any of (1) to (3), further including:
a strain measurement unit configured to measure strain of an object based on an ultrasound signal acquired from a vibrating element of the probe,
wherein the vibrator control unit sets the vibration parameter in accordance with a result of the strain measured by the strain measurement unit.

(5)

The ultrasound processing apparatus according to any of (1) to (4),
wherein the vibration parameter is a displacement, a vibration frequency, or a direction of a vibration.

(6)

The ultrasound processing apparatus according to (4) or (5), wherein the strain measurement unit synchronizes a timing of measurement of the strain with a vibration generated by the vibration generating unit.

(7)

The ultrasound processing apparatus according to any of (1) to (6), wherein a plurality of the vibration generating units are incorporated in the probe.

(8)

The ultrasound processing apparatus according to any of (1) to (6), wherein the probe is used in contact with an organ or a tissue during surgery.

(9)

An ultrasound processing method including:

setting, by a ultrasound processing apparatus, a vibration parameter of a vibration generating unit incorporated in a probe to vibrate the probe; and driving, by the ultrasound processing apparatus, the vibration generating unit based on the set vibration parameter.

(10)

A program for causing a computer to function as:

a vibration control unit configured to set a vibration parameter of a vibration generating unit incorporated in a probe to vibrate the probe; and a vibration driving unit configured to drive the vibration generating unit based on the vibration parameter set by the vibrator control unit.

REFERENCE SIGNS LIST 11 ultrasound diagnostic imaging apparatus
21 ultrasound probe
22 ultrasound signal processing unit
23 user interface
24 image display unit
31 vibrator
32 transducer
41 vibrator driving unit
42 vibrator control unit
43 transmission and reception separating unit
44 transmission BF unit
45 reception BF unit
46 strain computation unit
47 imaging signal processing unit
48 scan converter

The invention claimed is:

1. An ultrasound processing apparatus, comprising:
a probe that includes a vibration generator, wherein the vibration generator is configured to vibrate the probe based on a vibration parameter;
a vibration controller configured to:
set the vibration parameter of the vibration generator;
receive a reflected signal from an object corresponding to an ultrasound signal, wherein the reflected signal is acquired by the probe;
estimate a strain of the object based on the reflected signal;
change, based on the strain, the vibration parameter to synchronize a timing of the vibration generated by the vibration generator and a timing of detection of the strain; and
a vibration driver configured to drive the vibration generator based on the vibration parameter.

2. The ultrasound processing apparatus according to claim 1, further comprising a user interface configured to receive a user operation.

3. The ultrasound processing apparatus according to claim 2,
wherein the user operation corresponds to a focus position setting operation to set a user-specified focus position.

4. The ultrasound processing apparatus according to claim 1, wherein
the probe further includes a vibrating element configured to emit the ultrasound signal.

5. The ultrasound processing apparatus according to claim 1,
wherein the vibration parameter is one of a displacement of the vibration, a frequency of the vibration, or a direction of the vibration.

6. The ultrasound processing apparatus according to claim 1, wherein the probe comprises a plurality of vibration generators.

7. The ultrasound processing apparatus according to claim 1,
wherein, at a time of surgery, the probe is in contact with one of an organ or a tissue.

8. The ultrasound processing apparatus according to claim 1, wherein
the vibration controller is further configured to change a frequency of the vibration generated by the vibration generator to synchronize the timing of the vibration and the timing of the detection of the strain.

9. The ultrasound processing apparatus according to claim 1,
wherein the probe includes a transducer and a plurality of vibration generators including the vibration generator.

10. The ultrasound processing apparatus according to claim 9, further comprising a signal processor configured to:
determine a distance between a target point in a measuring area and the transducer; and
generate a detection signal by phase delayed addition of reflected signals corresponding to each of the plurality of vibration generators based on the determined distance,
wherein the vibration controller is further configured to set the vibration parameter based on the detection signal.

11. An ultrasound processing method, comprising:
in an ultrasound processing apparatus that comprises a probe including a vibration generator:
setting a vibration parameter of the vibration generator to vibrate the probe;
receiving a reflected signal from an object corresponding to an ultrasound signal, wherein the reflected signal is acquired by the probe;
estimating a strain of the object based on the reflected signal;
changing, based on the strain, the vibration parameter to synchronize a timing of the vibration generated by the vibration generator and a timing of detection of the strain; and
driving the vibration generator based on the vibration parameter.

12. A non-transitory computer-readable medium having stored thereon computer-readable instructions, which when executed by a computer, cause the computer to execute operations, the operations comprising:
setting a vibration parameter of a vibration generator to vibrate a probe, wherein the probe includes the vibration generator;

receiving a reflected signal from an object corresponding to an ultrasound signal, wherein the reflected signal is acquired by the probe;

estimating a strain of the object based on the reflected signal;

changing, based on the strain, the vibration parameter to synchronize a timing of the vibration generated by the vibration generator and a timing of detection of the strain; and driving the vibration generator based on the vibration parameter.

* * * * *